United States Patent [19]

Isakov et al.

[11] 4,069,823
[45] Jan. 24, 1978

[54] APPARATUS FOR LASER THERAPY

[76] Inventors: Viktor Leonidovich Isakov, ulitsa Fedorova, 1, kv. 67; Yan Yakovlevich Popov, ulitsa Yakira, 16/18, korpus 2, kv. 70; Boris Grigorievich Khlyvnjuk, ulitsa Moskovskaya, 5, kv. 38; Rostislav Evgenievich Kavetsky, ulitsa Vladimirskaya, 51/53, kv. 44; Nikolai Fedorovich Gamaleya, ulitsa Entuziastov, 3, kv. 153; Khadzhi Aminovich Baratov, ulitsa Fedorova, 9, kv. 5; Gennady Dmitrievich Krazhan, bulvar Lepse, 43, kv. 55; Ilya Romanovich Lazarev, prospekt 40-letia Oktyabrya, 126, kv. 88; Ivan Parfenovich Dedkov, ulitsa Kreschatik, 15, kv. 12; Alexei Ivanovich Krivenko, ulitsa Kamenyariv, 76/37, kv. 1; Vladimir Nikolaevich Dudnichenko, ulitsa Pushkinskaya, 41, kv. 2, all of Kiev, U.S.S.R.; Ivan Vasilievich Kudryavtsev, deceased, late of Kiev, U.S.S.R.; by Galina Antonovna Kudryavtseva, administratrix, ulitsa Suvorova, 13, kv. 108, Kiev, U.S.S.R.

[21] Appl. No.: 678,052

[22] Filed: Apr. 19, 1976

[51] Int. Cl.² ............................................. A61B 17/36
[52] U.S. Cl. ................................................. 128/303.1
[58] Field of Search ................. 128/303.1, 303 B, 395, 128/396, 2 R; 331/94.5

[56] References Cited

U.S. PATENT DOCUMENTS

| | | | |
|---|---|---|---|
| 3,061,936 | 11/1962 | De Dobbeleer | 128/303 B |
| 3,338,235 | 8/1967 | Gordon | 128/303 B |
| 3,348,547 | 10/1967 | Kavanagh | 128/303.1 UX |
| 3,528,424 | 9/1970 | Ayres | 128/303.1 |
| 3,566,872 | 3/1971 | Draeger et al. | 128/303.1 |
| 3,703,176 | 11/1972 | Vassiliadis et al. | 128/395 |
| 3,720,213 | 3/1973 | Hobart et al. | 128/303.1 |
| 3,769,963 | 11/1973 | Goldman et al. | 128/2 R |
| 3,796,220 | 3/1974 | Bredemeier | 128/303.1 |
| 3,910,276 | 10/1975 | Polanyi et al. | 128/303.1 |
| 3,914,013 | 10/1975 | Rosenberg | 128/303.1 |

Primary Examiner—Lawrence W. Trapp
Attorney, Agent, or Firm—Fleit & Jacobson

[57] ABSTRACT

Apparatus for laser therapy is designed for therapeutic and surgical action of laser emission upon tissue in clinical practice, as well as for wide application in a variety of medical and biological experiments. The apparatus comprises one or several lasers, a light guide to transmit the laser emission from a laser head to a particular point in the operation area, as well as a focusing barrel and/or a flexible light guide providing a means for irradiating or dissecting the tissue. The apparatus is provided, in accordance with the invention, with a scanning device featuring a focusing barrel and a flexible light guide and comprising at least two platforms for transverse and longitudinal travel in a horizontal plane with reflecting elements placed thereupon to permit transmission of the laser beam along the optical axis of the focusing barrel or the flexible guide, thus making it possible to combine in one apparatus irradiation by powerful laser emission and continuous laser emission for dissection of tissue in surgery.

16 Claims, 18 Drawing Figures

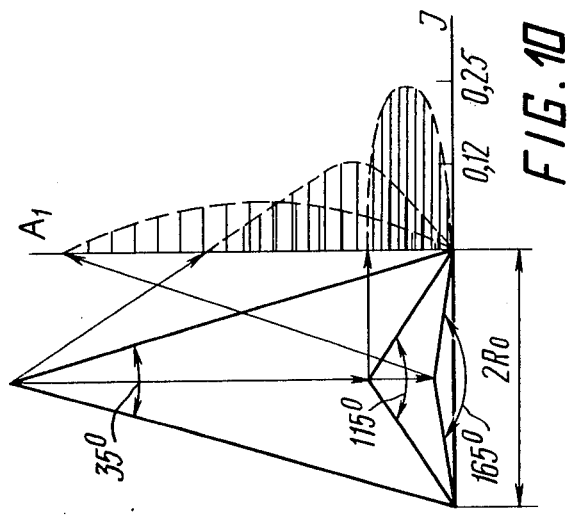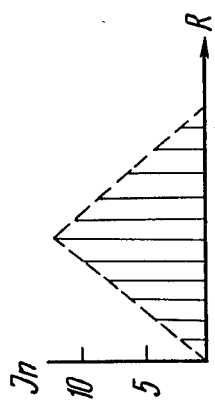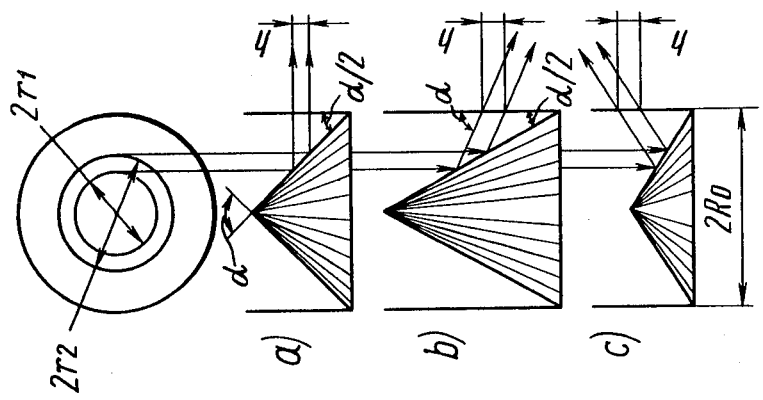

APPARATUS FOR LASER THERAPY

This invention relates to medical instruments and apparatus and, in particular, to apparatus for laser therapy intended for surgical and therapeutic treatment by laser irradiation in clinical practice, as well as for wide application in a variety of medical and biological experiments.

Specifically, the apparatus may be employed in oncology for local necrotization of tumor nodules by pulsed laser emission, for dissection and excision of tissue by CW laser beam in surgery, for selective sparing destruction of previously coloured pathological formations in dermatology, as well as in various other fields of clinical medicine. The apparatus may also be used in experimental medical and biological research for investigating the influence of pulsed and CW laser emission upon biochemical and cellular preparations, normal tissue and organs of laboratory animals, grafted tumors, etc.

Though the arrangements of existing clinical laser apparatus built around high-power pulsed and continuous-wave lasers are similar in many respects, including lasers proper with power units, control panels, light guides and focusing barrels, their designs differ greatly and are dictated primarily by the specific field of application.

Medical laser apparatus built around pulsed lasers are currently in clinical use essentially for therapeutic purposes, whereas apparatus built around CW lasers are for the most part used in surgery.

Employment of high-power pulsed lasers in clinical apparatus has called for radically new solutions of the problem of precise transmission of the laser beam to a particular point of the operation area providing for safety of the patient as well as medical and technical personnel.

Among medical laser apparatus currectly in use the apparatus of the U.S. Army Missile Command, Huntsville, Ala., installed at the National Health Institute in Washington, D.C. (Proceedings of the International Congresses on Medical and Biological Technology 1967, 1969, Chicago, U.S.A.) ranks as the most advanced and is close to the proposed apparatus in its characteristics and purpose. This apparatus comprises a pulsed neodymium laser with pulse energy reaching, 1,800 $j$, wave length $\lambda = 1.06$ mu, interval between energy pulses $t = 30$ sec. The emitting head of this laser is mounted upon a trolley. The light guide for transmission of the laser beam from the emitting head of the laser to a particular point in the operation area is rigidly connected to the emitting head and comprises tubular members coupled by means of at least two joints mounted on bearings. The hinges carry mirror reflectors of the laser beam and the last link of this light guide carries a telescopic focusing barrel. The focusing barrel may have attached thereto a plastic cone for trapping particles of the irradiated object, dispersed by the laser beam.

However, the design of this apparatus suffers from a number of disadvantages. The light guide for transmission of the laser beam from the emitting head to a particular point in the operation area is bulky and heavy, its tubular members are insufficiently flexible, and is inconvenient to operate because accurate aiming of the beam requires not only manipulation of the guide, but movement of the whole stand, whereon the laser head is secured, turning the laser head and moving it up and down. All this is a serious problem for the operator, prolongs the intervals between successive pulses of laser energy applied to the object of irradiation and, in general, tends to impair the characteristics of the apparatus, hence, the effectiveness of treatment.

The apparatus provides no means for accurate adjustment of the size of the focused laser beam on the object of irradiation and the protective cone secured on the focusing barrel hampers free manipulations of the laser beam within the operation area. Besides, the absence of a range finding device does not permit measurement of an accurate dose of laser energy incident upon the object of irradiation.

What is more, placing a high-power laser head directly in an operating room is dangerous for the personnel and the patient, particularly because of ionization and ozonization of the space around the laser head, liberation of noxious gases, and powerful noise accompanying the operation of a pulsed laser.

The design of the light guide employed in the apparatus for the transmission of the beam from the laser head to a particular point in the operation area does not permit the use of remote control of the irradiation process.

The best of the available laser devices for surgical operations is the apparatus designed by the American Optical Co (Laser Focus, 1967, No. 1, 12–15).

The apparatus comprises a high-power CW laser with a power unit, a flexible light guide to transmit the laser beam from the laser head to a particular point of the operation area, a support mounting the laser head. The light guide for transmission of the laser beam is secured to the laser head and comprises seven tubular members coupled by means of joints provided in these members. Each joint carries a reflector and the outlet tubular member mounts a focusing barrel. The apparatus features a power regulator and a laser beam simulation device.

Among the shortcomings of this apparatus are substantial loss of laser emission energy in the light guide when transmitting the laser beam from the laser head to a particular point of the operation area, complicated optical adjustment of the light guide, difficulties in accurately moving the focusing barrel in the operation area, heavy weight and large dimensions of the light guide because of excessive number of tubular members, inadequate safety of medical and technical personnel in the process of operation because the chosen arrangement of the apparatus involves placing of the laser head and high-voltage power units within the operation zone.

The forementioned clinical laser apparatus have, consequently, a number of disadvantages substantially reducing their efficiency when applied in practical medicine.

It is an object of this invention to provide an apparatus for laser therapy permitting both simultaneous and successive use of several lasers as well as wider range of laser beam manipulations during surgical operations and irradiation.

This object is achieved by that an apparatus for laser therapy having at least one laser with a power unit, a control system, an emitting head and a support mounting the laser head, a light guide to transmit the laser beam from the laser head to the specified point in the operation area, a barrel focusing the laser emission at a particular point of the operation area, comprises, in accordance with the invention, a scanning device placed after the laser downstream the laser beam permitting control of the latter in the operation area and comprising two reflectors positioned upon separate platforms of horizontal longitudinal and transverse travel, respectively, placed on perpendicularly arranged rails, the focusing barrel being mounted on the transverse travel platform.

The scanning device should preferably be provided with two more reflectors to offer wider freedom of manipulation by the laser beam during surgical operations, one of the reflectors being mounted on the longitudinal travel platform, and an additional transverse travel platform carrying the other one of said reflectors, the platforms being moved along the same perpendicularly arranged rails in a horizontal plane, the additional transverse travel platform mounting along the optical axis of the scanning device a flexible light guide delivering the laser beam to the prescribed point of the operation zone.

The flexible light guide may be made up of at least three cylindrical guides coupled by means of at least two joints secured therein on bearings, permitting pivoting of the guides about the optical axis, and accommodating reflectors of the laser beam arranged inside the joints upon alignment platforms attached to a lever-cam swinging mechanism of said reflector, a focusing device placed at the end of the last cylindrical light guide and detachable tips secured at the end of the focusing device facing the operation zone.

The flexible light guide should advisably be provided with a laser beam simulation system comprising a pulse source of visible light positioned in the cylindrical light guide and made in the shape of a ring.

The tip may be made as a truncated cone facing the object by its narrow end, whereas the junction of its wide end and the focusing device may be made as a parabolic ring, its inner surface having a mirror coating.

The additional transverse travel platform may be furnished with a locking device ensuring rigid connection with the main transverse travel platform.

For treatment of epithelial tissue of the viscera said tip may be made as a cylinder transparent for laser emission with a reflector placed therein and having a shape of a cone with its apex facing the incident laser beam, the apex angle of the cone being chosen depending on the energy density of the laser beam required for treatment.

When the apparatus comprises several lasers differing in their action on biological objects, an optical switch is to be placed at the point of intersection of their laser beams.

The focusing barrel may be made telescopic and furnished with an additional drive for vertical movement, as well as with a range finding device made in the form of a rule secured on the barrel and sliding thereon to measure the distance from the focusing lens of the barrel to the prescribed point in the operation area.

The apparatus may comprise a device to measure the laser beam energy, placed after the optical switch and comprising several series connected thermocouples positioned circumferentially to form a ring surrounding the laser beam.

For measurement of the CW laser emission the energy meter may be made as a rotating measuring device associated with a motor making it revolve, said measuring device being coupled to an indicator, its scanning being synchronized with the rotation of the measuring device by means of a synchronizer connected to said indicator and a motor power unit.

A switch may be inserted between the indicator and the measuring device to enable measurement of the distribution of energy density and power at any point of across the laser beam.

The measuring device should preferably be made as an annular holder with thermocouples stretched therein, their hot junctions being evenly distributed along the holder periphery and their ends being connected to current-conducting rings in their turn being in contact with a current collectors coupled to the commutator.

The apparatus may comprise an energy measuring calorimetric device for periodic monitoring measurements of the laser radiation energy, a part of the laser beam being deflected, during measurement, into the calorimetric measuring device by a dividing plate, e.g. translucent mirror, placed in the path of the laser beam.

The jounts of the flexible light guide may be furnished with at least two compensating springs, the ends of each of the springs being secured to the hinged cylindrical light guides.

The tip of the light guide should advisably be provided with a pipe union, sterile gas mixture being delivered therethrough to the point of contact of the laser beam with the biological object, thus creating a sterile zone around the operation area permitting more effective dissection of tissue and protecting the focusing device from fouling by products of interaction of the laser radiation with biostructures.

The apparatus should advisably be furnished with a suction system to remove the products of interaction of the laser radiation with biological structures of the object of irradiation, its flexible intake nozzles being directed to the operation area and connected with an air manifold by means of flexible hoses.

The apparatus may also be furnished with a television system, its camera being hinged to the scanning device and directed to the irradiated area.

The vidicon of the television camera may be provided with protective shutters furnished with an electro-mechanical drive and impervious to laser emission, these shutters covering the inlet aperture of the vidicon at the moment of the laser flash.

The invention will now be described in greater detail with reference to a specific embodiment thereof, taken in conjunction with the accompanying drawings, wherein.

Figure 11:
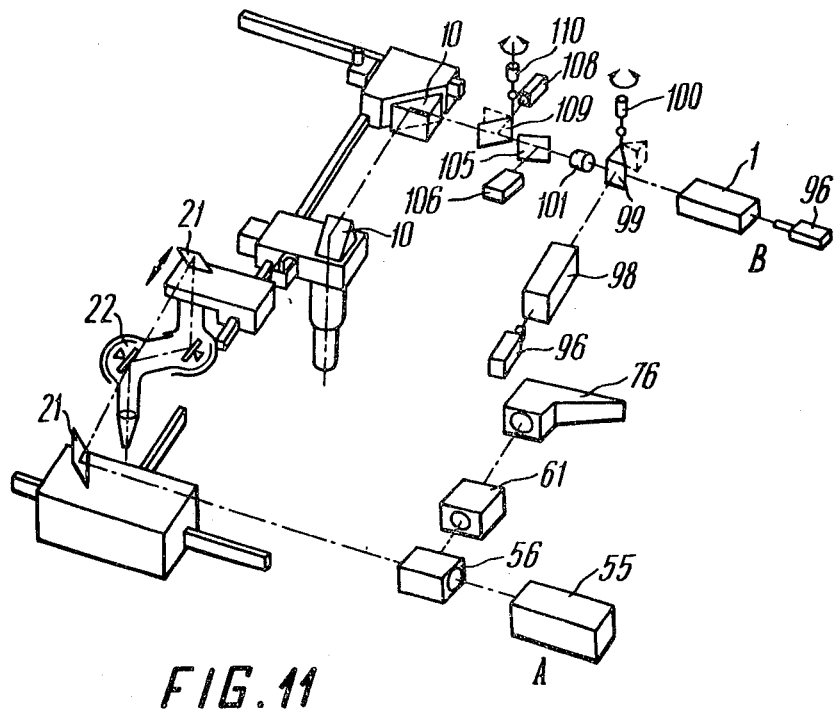
Figure 12:
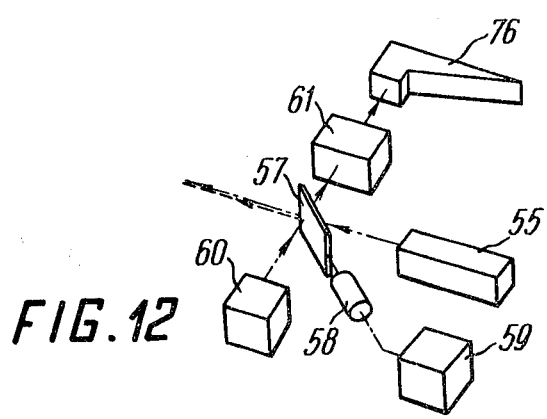
Figure 13:
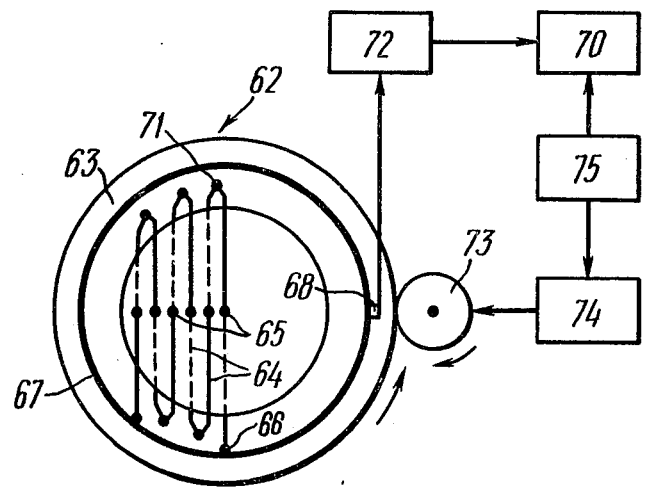
Figure 14:
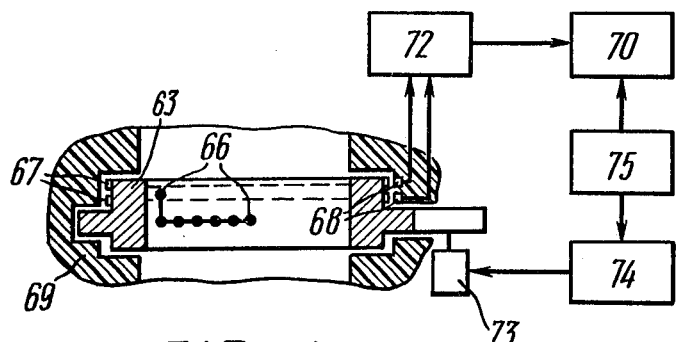
Figures 15, 16, 17:
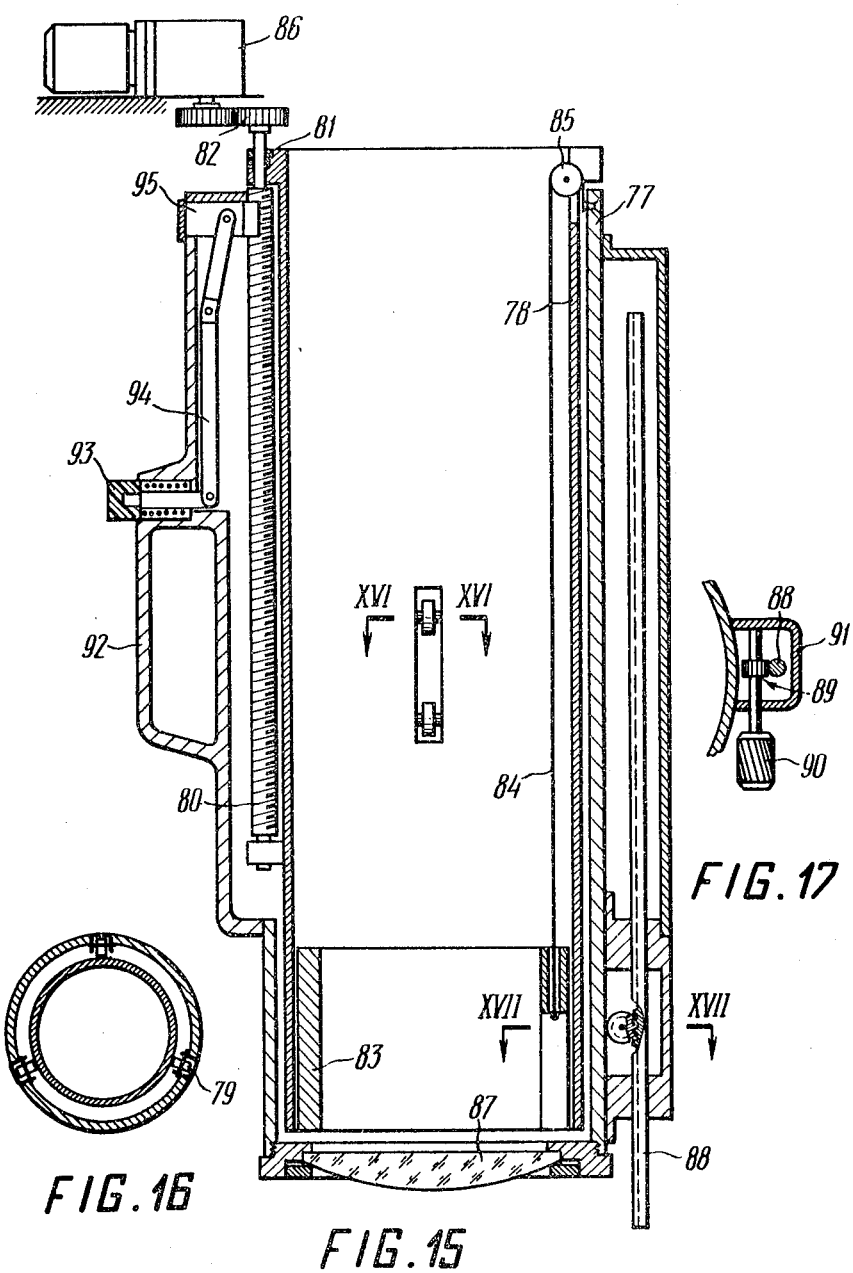
Figure 18:
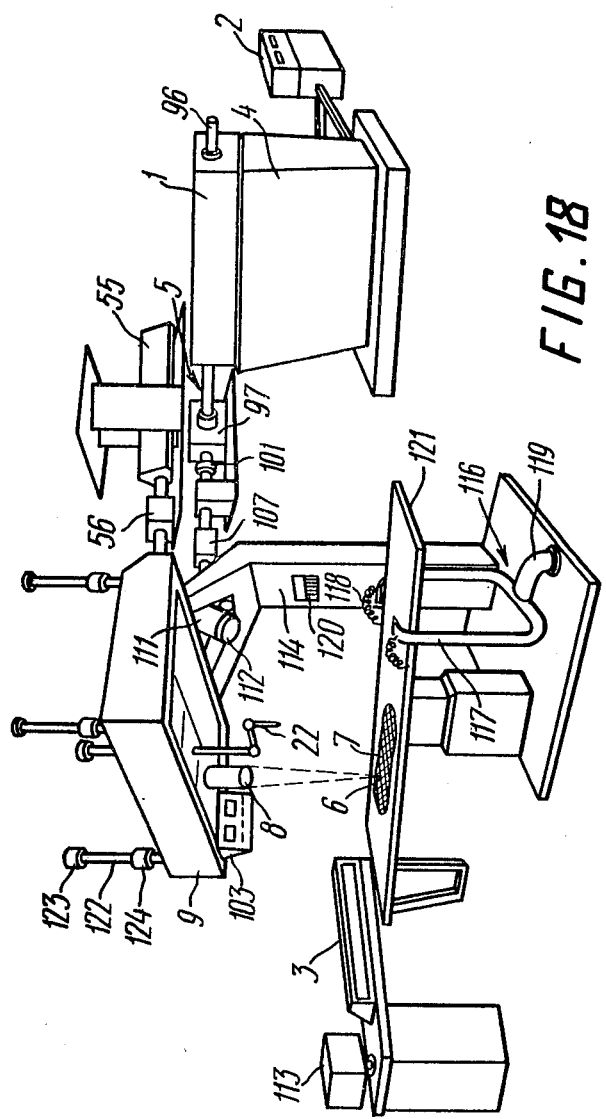

FIG. 8a,b,c shows the path of the laser beam when reflected from tapered reflectors with apex angles of 35°, 115°; 165°, according to the invention;

FIG. 9 is a graph illustrating the distribution of energy density of the laser beam, according to the invention;

FIG. 10 is a diagram of distribution of energy density of the reflected laser beam upon the cylindrical wall of the tip, according to the invention;

FIG. 11 is a general functional diagram of channels A and B, according to the invention;

FIG. 12 is a layout of elements in a part of channel A, according to the invention;

FIG. 13 is a block diagram of the CW laser radiation meter with a cross-section diagram of a measuring element, according to the invention;

FIG. 14 is a block diagram of a CW laser radiation meter with a longitudinal section diagram of the measuring element, according to the invention;

FIG. 15 is a schematic of the focusing barrel, according to the invention;

FIG. 16 is a sectional view taken along line XVI—XVI of the focusing barrel of FIG. 15, according to the invention;

FIG. 17 is a sectional view taken along line XVII—XVII of the drive of the range finding device of the focusing barrel of FIG. 15, according to the invention;

FIG. 18 is a general diagram of an apparatus for laser therapy, according to the invention.

The proposed apparatus for laser therapy comprises at least one laser I (FIG. I) with a power unit 2, a control panel 3, a support 4 carrying the head of the laser 1, a light guide 5 for delivery of the laser beam from the head of the laser 1 to a prescribed point 6 in an operation area 7, and a barrel 8 focusing the radiation of the laser 1 at this point.

Figure 2:
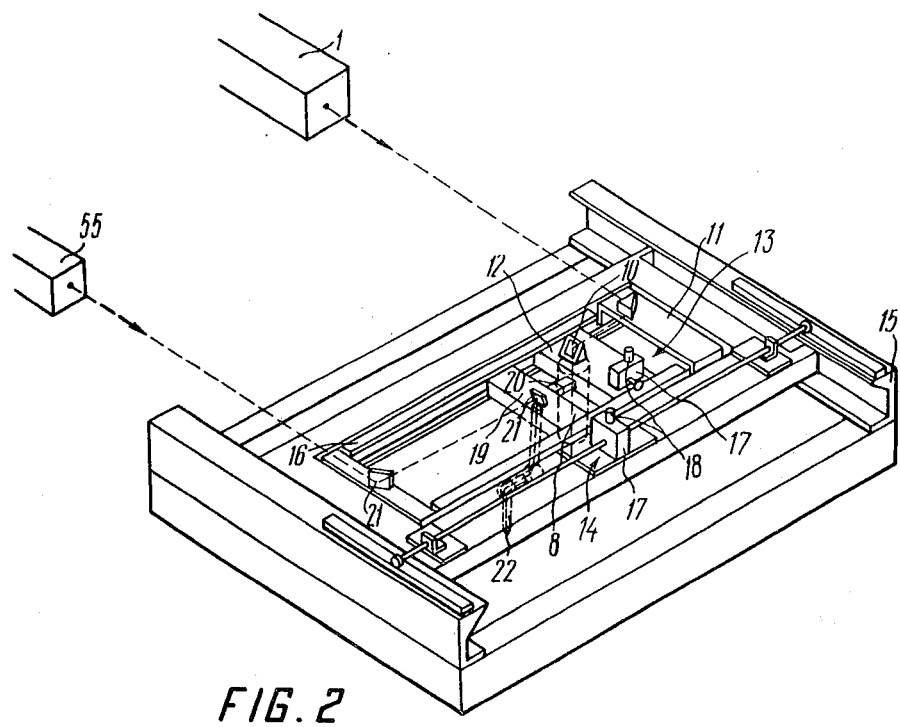
FIG. 2 is a simplified diagram of the scanning device of the apparatus for laser therapy according to the invention.

The proposed apparatus comprises, in accordance with the invention, a scanning device 9 placed after the laser I downstream of the laser beam, permitting control of the laser beam in the operation area 7, and comprising two reflectors 10 (FIG. 2) positioned on separate main platforms 11 and 12 of longitudinal and transverse travel, respectively, moving in a horizontal plane with the help of respective drives 13 and 14 along perpendicularly arranged rails 15 and 16.

The drives 13 and 14 in the proposed apparatus may be electromechanical drives, each of them having a cylindrical worm gear reducer 17 with a step motor 18.

The focusing barrel 8 is mounted on the main transverse travel platform 12.

However, clinical practice demonstrates that it is not infrequent when several lasers are employed simultaneously or successively.

In this case, the apparatus is furnished with an additional platform 19 for transverse travel moved along rails 16 by either the drive 13 or by hand, without a drive. Engagement or disengagement of the platforms 12 and 19 is effected by a lock 20.

The dual movement capability of the platform 19 permits, when operated manually, reduction of effort of the surgeon's hand during operations by excluding the effort to move the main platform 12 with the drive 13 and, when the main platform 12 and the additional platform 19 are engaged, remote simultaneous or successive switching of at least two lasers.

Figure 1:
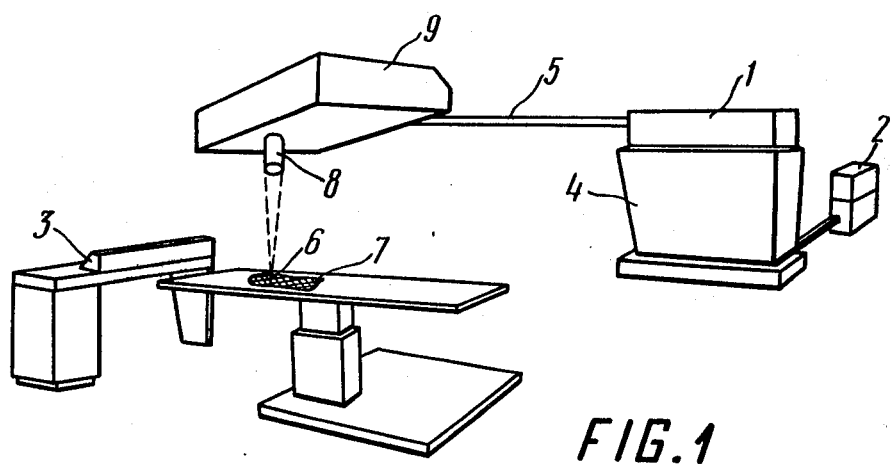
FIG. 1 is a schematic general view of an apparatus for laser therapy, in accordance with the invention.

Two additional reflectors 21 for control of the laser beam in the operation area 7 (FIG. 1) are mounted on the main transverse travel platform II and the additional transverse travel platform 19 moving in a horizontal plane on the same perpendicular rails 15 and 16 with the help of the electromechanical drives 13 and 14.

A flexible light guide 22 delivering the laser beam to the prescribed point 6 is mounted on the additional platform 19.

The forementioned suggests that the emission of the lasers I may be delivered to the scanning device 9 of the proposed embodiment by two paths: channel A and channel B.

The two-channel design of the scanning system ensures control of simultaneous or successive operation of several lasers and substantially widens the application of this apparatus in various fields of medicine. Among the advantages of this embodiment of the apparatus are: irradiation of different parts of a patient's body in the course of one surgical operation without moving him, increased accuracy of bringing the laser beam to the prescribed point and scanning of the laser beam in the operation area by means of the electromechanical drive, as well as simultaneous or successive operation of two channels of the scanning device.

In the description of the design of the proposed apparatus that follows, first comes the description of the channel A, then the channel B.

The part of the channel A comprising the two reflectors 21 (FIG. 2) and the flexible light guide 22 will be identified as the laser knife channel of the scanning system 9 because the laser beam passing therethrough comes to the flexible light guide 22 permitting free manipulations by the laser beam in the operation area 7 and, consequently, it may be used to dissect tissue in surgical operations. At the same time, the part of the channel B comprising two reflectors 10 and the focusing barrel 8 is most commonly used for delivery of powerful laser emission to irradiate localized surfaces of uncovered tissue or live tissue to a certain depth by a focused laser beam. That is why, this part of the channel B will be referred to, for simplicity, as the therapeutic effect channel.

It should be noted, however, that the proposed classification is somewhat conventional because by the use of low-powered or unfocused laser beams travelling along the channel A therapeutic effect and not dissection of tissue can be obtained.

Figures 3, 4:
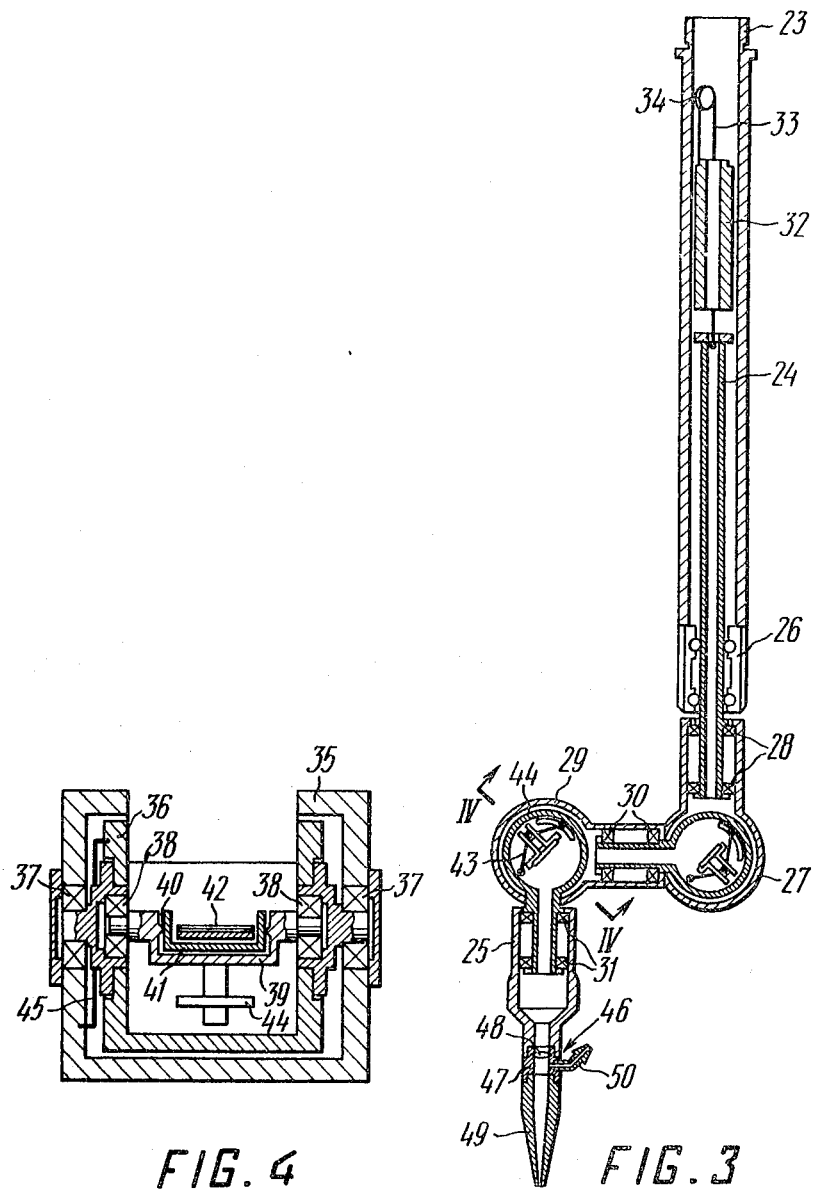
FIG. 3 is a diagram of the flexible light guide, according to the invention.
FIG. 4 is a schematic view of a flexible guide joint, taken along line IV—IV, according to the invention.

In this embodiment, the flexible light guide 22 (FIG. 2) for accurate delivery of the focused laser beam to the prescribed point 6 of the operation area 7 is made as hinged hollow cylindrical light guides 23, 24, 25 (FIG. 3). The cylindrical light guide 24 is located inside and coaxial to the cylindrical light guide 23, bearings 26 permitting axial movement of the light guide 24 in relation to the light guide 23. A joint 27 is mounted on the light guide 24 on bearings 28 and a joint 29 is mounted on bearings 30 resting by their inner races upon the joint 27. The light guide 25 is similarly secured to the joint 29 mounted on bearings 31.

The flexible light guide means, with the exception of the cylindrical light guide 23, is counter-balanced by a weight 32 connected by a wire 33 to the light guide 25. Bending of the wire 33 is ensured by a deflecting roller 34.

The joints 27 and 29 comprise an outer casing 33 and an inner casing 36 (FIG. 4), the casing 35 being adapted to rotate in relation to the casing 36 on bearings 37.

A connecting link 39 is mounted on bearings 38 in the inner casing 36, an alignment platform 41 being set upon pins 40 and a reflector 42 being attached thereto. Arms 43 are hinged to the outer casing 35 and the inner casing 36 (FIG. 3), their other ends being hinged to a slide 44 (FIG. 4) moving in the slot of the connecting link 39.

The mass of the inner casing 36 is balanced in relation to the outer casing 35 by a spiral spring 45, its ends being fixed in the outer casing 35 and the inner casing 36.

The cylindrical light guide 25, placed in the light guide 22 last in relation to the laser, is connected to a focusing device 46 comprising a holder 47 with a lens 48 secured therein. A tip 49 is in turn secured to the focusing device 46 ensuring screening of laser radiation and protection of surgeon's hands against inadvertent contact with the laser beam. The material and basic characteristics of the lens 48 depend upon the type of laser employed and medical application. Thus, when a $CO_2$ laser with a wavelength of 10.6 mu is employed, the lens is made either of sodium chloride (NaCl) or of germanium (Ge), whereas lenses for visual wavelength lasers are made from glass or quartz.

To obtain laser beams of small diameters for dissection of tissue, it is recommended that the focusing device be furnished with biconvex lenses with a focal distance of 80–100 mm.

With the outer diameter of the lens reaching 15–16 mm, the minimum size of the laser beam spot is 0.1 mm in diameter and it becomes possible, with a laser beam density of $5 \cdot 10^5$ w/sq.cm., to make narrow discussion up to 10 mm deep at a rate of 1 cm/sec.

To apply an unfocused layer beam to tissue, the lens 48 of the focusing device is either removed or tissue is irradiated by the laser beam at a distance longer than its focal distance.

The choice of a lens sets certain requirements to the choice of a tip which may be of different designs. The proposed apparatus employs hollow metal tips 49 shaped as a hollow truncated cone. In some cases massive cone tipes made of a dielectric material, e.g. glass or quartz, may be recommended, as well as "faux cones" which make it possible to do without lenses at all.

Let us consider, by way of example, several embodiments of tips which may be mounted in the flexible light guide 22 depending on the object of laser use in surgical operations.

One of the embodiments of the tip 49 illustrated in FIG. 3 may be recommended for use with the focusing lens 48 made of a material (NaCl) transparent for measurements of the visible part of the wavelength range. In this case, the tip 49 is furnished with a pipe union 50 (FIG. 3) for supply of a sterile gas mixture to protect the focusing lens 48 against fouling by the products of laser radiation interaction with live tissue, primarily against water vapours produced by evaporation of biostructures because the lens made of NaCl is highly water-absorbing. The proposed arrangement of the tip with a lens of NaCl permits quite a simple solution of the problem if visualization of invisible infrared laser emission by making the simulating light beam coincide with the laser beam on the optical axis of the flexible light guide 22 and by focusing this light beam with the help of the same focusing lens 48, thus permitting the surgeon to accurately aim the invisible laser beam to the required point.

Figure 6:
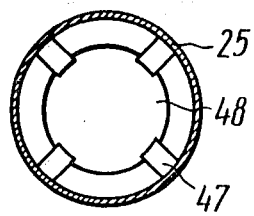
FIG. 6 is a cross-section view of the focusing device of the light guide, taken along line VI—VI, according to the invention.

Another embodiment of the tip 49 (FIG. 5) is designed for use with the lenses 48 of germanium (Ge) completely impervious for the visible light. For visualization of the invisible laser beam the upper part of the tip 49 is made as a ring 51, its inner surface being mirror-coated and forming a two-mirror reflecting system with the surface of the lens 48 intended for focusing the visible light coming into the clearance between the inner cylindrical surface of the light guide 25 (FIG. 6) and the lens 48 (FIG. 6). A visible light source 52 made as a ring is placed in the cylindrical light guide so that its light falls on the ring 51 and the lower surface of the lens 48 and is focused in the focus of the lens 48. Laser radiation is simulated with the help of flash lamps, e.g. annular xenon flash tubes, permitting reduction of the threshold intensity of illumination of the simulation source required for reliable location of the laser beam position in the operation area 7 taking into consideration the high level of illumination intensity demanded by surgical operations conditions. The use of the proposed simulation system provides a means for reduction of both the simulation sources and their dimensions.

Figure 7:
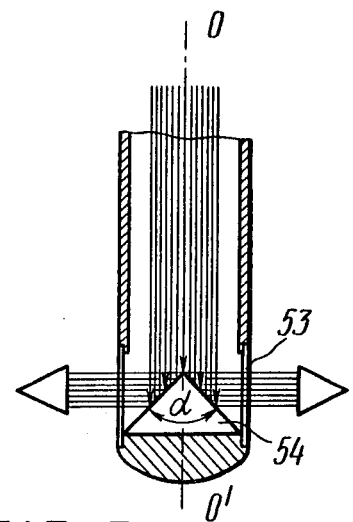
FIG. 7 shows an embodiment of a tip with the reflector made as a cone, according to the invention.

The design of the tip 49 is modified for irradiation of epithelial tissue of the viscera, since the concentrated laser beam is to be transformed into a diverging cylindrical beam. An embodiment of the tip 49 (FIG. 5) to comply with the requirement is shown in FIG. 7. The tip is made as a hollow cylinder, its walls being transparent for laser light. A reflector 54 is mounted inside and made as a cone with the point directed to the incident beam. The path of the laser beam is shown by arrows in FIG. 7. The choice of the apex angle depends on the requirements of redistribution of the laser beam energy.

Proceeding from the condition of even distribution of energy over the cross-section of the laser beam, a formula may be obtained to determine the energy distribution on the side wall of the tip.

$$P = \frac{r_2 + r_1}{2R} \cdot \frac{tg\,\alpha \cdot tg\frac{\alpha}{2}}{tg\,\alpha - tg\frac{\alpha}{2}}$$

where
R is the radius of the laser beam,
$\alpha$ is the reflector apex angle,
$r_1$, $r_2$ are selected radii of the laser beam ($r_2$, $r_1 < R$).
When the tip 49 is replaced in the flexible light guide 22 (FIG. 2), wherein the reflectors 54 (FIG. 7) with different apex angles are used, it is not only the angle of the reflected laser beam in relation to the optical axis OO (FIG. 7) that is changed, but also the height h (FIG. 8) of the cylindrical surface of the tip, the total laser reflected beam falling thereupon, is changed too. The relation between the laser beam cross-sectional area before reflection from the reflector 54 and the cylindrical surface area of the tip with the height h is the transformation coefficient which determines the redistribution of the energy density of the laser beam (FIGS. 9 and 10).

If the pattern of distribution of the laser beam energy density over its cross-section is known, the diagram of distribution of energy on the cylindrical wall of the tip 53 (FIG. 7) may be obtained with the help of the transformation coefficient. The triangular pattern of distribution of the laser beam energy density over its cross-section shown in FIG. 9 was chosen as an example and, proceding from that, the transformed energy density on the side wall of the tip was calculated for three angles $\alpha$ equal to 35°, 115° and 165°, the results being demonstrated in FIG. 10.

With this embodiment of the tip, the lens 48 of the focusing device may be removed or replaced with a more long-focus or short-focus lens depending on the requirements of the additional transformation of the laser beam. The flexible light guide 22 (FIG. 2) featuring the tip of this design is of certain interest for therapeutic application in gynecology, otolaryngology, surgery, etc.

The channel A comprises, apart from forementioned devices of the laser knife channel, at least one laser 55 (FIG. II) and an optical switch 56.

The laser 55 is selected depending on medical application. For dissection of tissue, the mean or continuous wave radiating power of lasers is to be 40–70 W. $CO_2$ lasers are most frequently employed for this type of operations. As stated above, however, other lasers with an output of less than 1W may be used instead of more powerful ones when tissue is not dissected but irradiated for therapeutic effect. The design of the scanning device permits the use of any laser without rearrangements. The proposed apparatus may, therefore, serve not only for surgery and therapy, but also for a wide range of physical and medical experiments.

The optical switch 56 (FIG. II) comprises a reflector 57 (FIG. 12) placed downstream of the laser beam in the channel A at an angle of 45° to the laser beam. The reflector 57 is connected with an electromechanical drive 58 controlled by the operator himself with the help of a pedal 59. When the laser beam is blocked, the reflector 57 directs the simulating beam from a simulation device 60 along the channel A to aim the flexible light guide 22 (FIG. 3) to the prescribed point 6 (FIG. I) of the operation area 7 (FIG. I) without the danger of hurting healthy tissue by the laser beam.

A measuring device 61 (FIG. 12) serves to measure the continuous emission of the laser and comprises a measuring member 62 (FIG. 13) incorporating an annular holder 63, e.g. a revolving ring, wherein a number of thermocouples 64 is secured so that their hot junctions 65 are placed along the periphery of the ring hole, the laser beam being passed therethrough. Any types of thermocouples may be installed in the ring holder 63. One of the embodiments of the proposed measuring device uses wire junctions made from Chromel drops 0.05 mm in diameter. Such thin wires are employed to reduce the drift of the device and the disturbance of the laser beam caused by thermocouples and are fixed by their ends on opposite sides of the hole of the ring holder 63 (FIG. 13) so that they serve at the same time as braces securing the hot junctions 65 of the thermocouples 64 in relation to the center of the hole of the holder 63 and, consequently, to the laser beam. The thermocouples 64 (FIG. 13) contact by their ends 66 conductors made as separate and isolated from one another current-conducting rings 67 placed on the outside of the holder 63. Each of the rings 67 contacts a current collector 68 secured in the casing of a fixed holder 69 and connected by a cable to an indicator 70 which may be any one of such instruments as microammeters, automatic recorders, oscillographs with long persistence, etc. When measuring the laser emission, the proposed instrument permits measurement of the laser beam power in different ways: to measure the total radiating power of the laser beam, to determine the distribution of energy density of the laser emission across the beam, to measure the power at any across the beam, etc.

When the total power of the laser beam is measured, the thermocouples are connected in series as illustrated in FIG. 13 so that their cold junctions 71 are placed in the casing of the ring 63 forming together with the hot junctions 65 a thermopile, its ends being electrically connected via the current-conducting rings 67 and the current collectors 68 to a switch 72. In this case, only two current-conducting 67 are secured on the ring holder 63.

When the distribution of energy density and power at any point across the laser beam are measured, the outer surface is provided with a double number of rings in relation to the number of the thermocouples 64 (FIG. 13) and the signals from the current collectors 68 are fed to the switch 72 which may, in the simplest case, be a multi-wavered switch ensuring commutation of the thermocouples 64 (FIG. 13) in all modes of the measuring device operation. To reduce the number of thermocouples in the proposed apparatus the hot junctions 65 of the thermocouples 64 are scanned across the laser beam by revolving the ring holder 63 about its axis. Each of the hot junctions 65 is positioned at a certain distance from the hole center of the ring holder 63 and, when rotated, each hot junction 65 describes a circle in the plane of the beam cross-section, spaced from the laser beam center at a distance separating the hot junction from the center of the hole of the ring holder 63. When rotated, the thermocouples 64 ensure successive measurement of the laser beam power at every point of these circles. The ring holder 63 is rotated by means of a motor 73, its operation being synchronized with the scanning of the indicator 70 by feeding synchronizing pulses from a synchronizer 75 to a power unit 74. At the same time, these synchronizing pulses are supplied to the indicator 70. The use of such a measuring device helps the surgeon to control the laser energy dose during the operation and make hig choice as to the optimum mode of laser operation in the course of irradiation.

A trap 76 (FIG. 12) is placed after the measuring device 61. When the surgeon uses the simulated beam during preparation for dissection of issue and the laser beam is not to penetrate the operation area, the reflector 57 is set by the drive 58 controlled by the pedal 59 across the laser beam path at an angle of 45° C. The laser beam is reflected by the reflector 57 and comes into the trap 76 wherein after multiple reflections from the trap walls it is dispersed and absorbed inside the trap. Any design may be employed as long as it satisfied the "black box" conditions. The proposed apparatus makes use of a wedge structure with an output apperture of 20 mm and 180 mm long as one of the possible variants.

The channel B of the therapeutic effect of the proposed apparatus features the focusing barrel B (FIG. 1), preferably of a telescopic type, intended for accurate delivery of the laser beam to the prescribed point 6 (FIG. I) in the operation area 7 (FIG. I) and beam focusing therein. The main members of the telescopic barrel (FIG. 15) are two hollow metal cylinders, one cylinder 77 and an inner cylinder 78.

The outer cylinder 77 rests on bearings 79 (FIG. 16) when the inner cylinder 78 is moved. A drive screw 80 on bearings 81 is mounted in the inner cylinder 78. A gear 82 is secured to one of the ends of the drive screw.

The telescopic focusing barrel also comprises a balance weight 83 suspended inside the inner cylinder 78 on flexible cables 84, their second ends being secured on the outer cylinder 77. A deflection roller 85 is placed at the bend of the cables. The telescopic focusing barrel is furnished with an electromechanical drive 86 for remote control. The outer cylinder 77 features a detachable focusing lens 87 and the outer surface of the barrel 8 (FIG. I) carries a range finding device comprising a sliding rule 88 with a scale (FIG. 15a), a drive 89 of the rule (FIG. 17), a handle 90, and a case 91. The outer cylinder 77 is provided with a handle 92 (FIG. 15) serving at the same time as a housing for a button 93 and a spring of a lever drive 94 of a split nut 95. The channel B has at least one laser I (FIG. I) with an alignment low-power laser 96 (FIG. 18). When two or more pulsed lasers are used, an optical switch 97 (FIG. 18) is placed in the point of their laser beams intersection to ensure alternate commutation of emission of the lasers 1 and 98 (FIG. II) during an interval between pulses.

The optical switch 97 comprises a reflector 99 (FIG. II) placed on a turntable actuated by an electromechanical drive 100.

Arranged downstream of the beam in the channel B is a laser energy meter 101 made as a pile of thermocouples positioned in a ring along the perimeter of the laser beam. The readings of the laser energy meter are provided by instruments on a surgeon's panel 103 (FIG. 18) and the central control panel 3.

Periodic calibrations of energy parameters of the lasers 1 and 98 (FIG. II) are done with the help of a reference measuring instrument 106 of a calorimetric type, a part of the laser beam being deflected thereinto by means of a dividing plate 105 set in the path of the beam.

The scanning device 9 (FIG. 18) is preceded by a laser beam simulation system 107 comprising a pulsed visible light source 108 (FIG. II), a sliding reflector 109 directing the laser beam simulation light along the channel B.

The simulation system 107 (FIG. 18) is provided with an electromechanical drive 110 (FIG. II) controlling the position of the reflector 109 to synchronize the pulsed operation of the laser I and the system 107.

A television system is provided for watching the progress of the operation and comprises a camera III (FIG. 18) with a vidicon 112, a monitoring device 113 with power supply and control units (not shown).

The camera III directed to the operation area 7 is mounted on a stand 114 and hinged to the scanning device 9. Besides, the camera features a mechanism 112 to shut off the vidicon, comprising protective shutters with an electromechanical drive. The shutters are impermeable to laser light and close the inlet port of the TV camera 111 at the moment of the laser flash.

The monitoring device 113 of this system is placed on the central control panel outside the operation room.

To remove the products of interaction of the laser emission with biological structures of the object of irradiation the apparatus is furnished with a suction system 116 (FIG. 18) comprising special intake nozzles 117 secured on flexible brackets 118 and an air manifold 119 connected with the intake nozzles by means of flexible hoses (not shown).

The operating room is also furnished with an intercommunication system 120 arranged in the support 114 used to suspend the scanning device 9 over a surgical table 121 at a height convenient for the surgeon. Sometimes the scanning device may be suspended from the ceiling by brackets 122 and flanges 123 and its elevation over the table is adjusted by turnbuckles 124.

The surgeon's panel 103 is mounted on the scanning device 9 (FIG. 18) and comprises all lasers control and monitoring members.

The proposed apparatus operates as follows.

The emission of the lasers I and 55 (FIG. 2) is delivered separately along two channels A and B (FIGS. II and 2) to the scanning device 9 (FIG. I), the emission of the laser 55 going along the channel A and the emission of the laser I passing along the channel B. Should the need arise to employ more lasers, the proposed apparatus permits an increase of their number by delivering the emission of additional lasers into the channel A or B and orienting the direction of these lasers emission along the optical axes of the channels A or B, respectively, with the help of the optical switches 97 (FIG. 18). The principle of operation of such a switch is shown in FIG. 11 for the channel B comprising the reflector 99 placed on a travelling platform and the electromechanical drive 100. In such a way the emission of the laser 98 (FIG. II) is fed to the scanning device 9 (FIG. I).

Combining several lasers 55, I, 98 (FIG. II) in one apparatus, control of their simultaneous or alternate operation, as well as mobility of manipulations in the operation area 7 (FIG. I) and focusing in the prescribed point 6 (FIG. I) of this area 7 (FIG. I) of emission of all lasers ensure a wide range of application for the proposed apparatus in scientific medico-biological as well as physical and medical experiments.

Before dealing in detail with the operation of each of the channels A and B of the proposed apparatus, let us consider its modes of operation.

Provision is made for the apparatus to operate in two modes, their choice being dependent upon the nature of the operation to be performed and presence of the surgeon and personnel in the operating room.

The first mode is used when the surgeon is present in the operating room. In this case, the apparatus is controlled from the surgeon's panel 103 (FIG. 18). The patient is placed on the operating table 121 with the operation area 7 turned in the direction of the scanning device 9. The focusing barrel 8 is moved to the region over the operation area 7 (FIG. I) with the help of the basic longitudinal travel platform II and the transverse travel platform 12 (FIG. 2) by means of the drives 13 and 14 along the perpendicularly arranged rails 15 or 16 or manually. The scanning device 9 (FIG. 18) is, in the first instance, controlled from the surgeon's panel 103 or the central control panel 3. Radiation of the light source 108 (FIG. II) simulates the laser emission in the course of introduction of the focusing barrel into the region over the operation area 7 (FIG. I), adjustment and focusing of the lasers I and 98 (FIG. 11) to the prescribed point 6 (FIG. 18) of the operation area 7.

Several characteristics of the laser emission are to be known during irradiation, their value being set by the surgeon on the basis of analyses of additional information. This primarily applies to the density of emission energy in the prescribed point 6 (FIG. I) of the operation area 7 (FIG. I), which depends on the size of the irradiated area and the energy of the laser beam. Adjustment of the laser beam diameter in the channel B set in the prescribed point 6 is effected either manually or by the electromechanical drive 86 (FIG. 15) by lifting or lowering the focusing barrel 8 (FIG. 18) and the operating table 121, whereas adjustment of the beam diameter in the channel A can be done by hand only by lifting or lowering the cylindrical light guides 24 (FIG. 3) relative of the flexible light guide 22 (FIG. 2), as well as by changing the angles between the cylindrical light guides 23, 24, 25 (FIG. 3) by turning the joints 27 and 29. The distance from the focusing lens 87 (FIG. 15) of the focusing barrel 8 (FIG. 18) to the operation area 7 is measured with the help of the sliding rule 88 (FIG. 15).

Coincidentally with the adjustment of the focusing barrel 8 (FIG. 18) and the flexible light guide 22 of the scanning device preparation of the lasers 55, I and 98 (FIG. 11) for work is performed, by switching on their power units, the camera III and the monitoring device 113 (FIG. 18) of the television system (FIG. 18), the air suction device 116, the intercom 120. Then the pulsed lasers are pumped to the required energy level and started (fired) to obtain a laser flash.

The work of the lasers and their energy characteristics during pumping and radiation are controlled by the surgeon from his control panel 103 (FIG. 18).

The process of irradiation may be watched by means of the television system (FIG. 18), on the screen of the monitor 113 (FIG. 18) disposed on the control panel 3. The vidicon shut-off mechanism 112 is actuated at the moment of the laser start, that is when laser pulsed emission passes and interacts with biological structures, and its photocathode is protected against damage by the reflected laser light.

When operating the lasers of the channel A, the vidicon shut-off mechanism is not employed because this channel is usually for CW lasers and the part of their emission reflected from biological structures falling upon the photocathode of the vidicon does not damage it.

The second mode of the proposed apparatus work implies that the surgeon and servicing personnel stay in the operating room only to prepare the patient for the operation and adjust the scanning device and other auxiliary systems. The apparatus is controlled and monitored in the process of operation from the control panel 3 (FIG. I) comprising control, monitoring and indication elements.

Let us deal in detail with the work of each of the channels A and B of the proposed apparatus.

Channel A (FIG. II)

The laser 55 (FIG. II) is carefully aligned before being switched on so that the laser emission coincide with the optical axis of the channel A. After the laser 55 is started, its emission falls on the optical switch 56 (FIG. II) and more exactly on its reflector 57 (FIG. 12) made of emission-reflecting materials and positioned at an angle of 45° to the optical axis of the channel A. When $CO_2$ laser with a wavelength of 10.6 mu is employed, the reflector may be a gold-coated steel plate with a reflection factor of 98%.

The reflector 57 may be in either "on" or "off" position. When switched on, the reflector 57 shuts off the beam of the laser 55 and directs it to the measuring device 61, whereas when switched off, the reflector 57 is removed from the channel and lets the beam of the laser 55 to the scanning device 9 (FIG. I).

The reflector 57 is connected to the electromechanical drive 58 controlled by the surgeon with the help of the pedal 59 (FIG. 12). When the reflector 57 is on, the simulating beam of the simulation device 60 (FIG. 12) falls on the second surface of the reflector 57 and is directed instead of beam of the laser 55 along the channel to the scanning device 9 (FIG. 1) and simulates the beam for adjustment and alignment of the apparatus.

The beam of the laser 55 (FIG. 11) comes, after being reflected from the reflector 57 (FIG. 12), into the hole of the ring holder 63 of the measuring member 62 (FIGS. 13 and 14). A part of this beam falls on the thermocouples 64 placed in this hole, but the major part of the beam passes into the trap 76 (FIG. 12) positioned after the measuring member 62 (FIG. 13) and the beam is dispersed and absorbed after multiple reflections therein. The part of the beam incident upon thermocouples is to a certain extent reflected, dispersed and absorbed, thereby resulting in appearance of a thermal e.m.f. The thermocouples are connected in series into a thermopile and the current of all thermocouples is added. The total current passes via the current conducting rings 67 (FIG. 14) and the current collectors 68 to the commutator 72 and then to the indicator 70.

When power is to be measured at each point across the laser beam or the density of energy is to be determined across the beam, each of the thermocouples 64 is connected to two current-conducting rings 67 and two current collectors 68 connected, in turn, via a cable to the switch 72.

The ring holder 63 of the of the measuring member is rotated by the motor 73, its work being synchronized with the operation of the indicator 70 by feeding synchronization pulses from the synchronizer 78 to the power unit 74 of the motor 73 and the indicator 70. It should be noted that both measuring and simulation of the laser beam takes place when the beam itself is shut off by the reflector 57 (FIG. 12), that is while the surgeon is preparing for the operation and has to check the performance of the apparatus. When the surgeon passes the pedal 59, the reflector 57 assumes the position to pass the laser beam to two additional reflectors 21 (FIG. I) placed on the additional transverse travel platform 19 (FIG. 2) and the main longitudinal travel platform II and is directed into the flexible light guide 22. As stated above, the platforms II and 19 are moved in a horizontal plane on the perpendicular rails 15 and 16 either by means of the electromechanical drives 13 and 14 or manually. The platforms 12 and 19 may be separated by disengaging the lock 20 which substantially relieves the surgeon's hand during manual operation by reducing the load to be moved.

The beam of the laser 55 coming into the flexible light guide 22 passes along the hollow cylindrical light guides 23 and 24, reflects from the reflectors 42 (FIG. 3) and enters the cylindrical light guide 25, falls on the focusing lens 48 (FIG. 3) and is delivered via adjacent tips 49 to the prescribed point 6 (FIG. I) of the operation area 7 (FIG. I). In the course of operation, the laser beam is at all times directed precisely along the optical axis of the channel A (FIG. 11) with the help of the reflectors 42 whatever the angle between the cylindrical light guides 23, 24 and 25 (FIG. 3) and the joints 27 and 29.

The design of the flexible light guide 22 permits mutual movement of the hollow cylindrical light guides 23 (FIG. 3) and 24 in axial direction on the bearings 26. The cylindrical light guide 24 rotates about its axis on the bearings 28. Rotation of the joints 27 and 29 and the cylindrical light guide 25 is effected on the bearings 28, 30 and 31 (FIG. 3).

The alignment platforms with the reflectors 42 are pivoted on the bearings 38.

The unbalanced masses of the light guide 24 are compensated automatically by the weight 32 suspended on the wire 33 via the deflecting roller 34 to the light guide 24, whereas the unbalanced mass of the inner casing 36 of the joints 27 and 29 is compensated by the spring 45.

Figure 5:
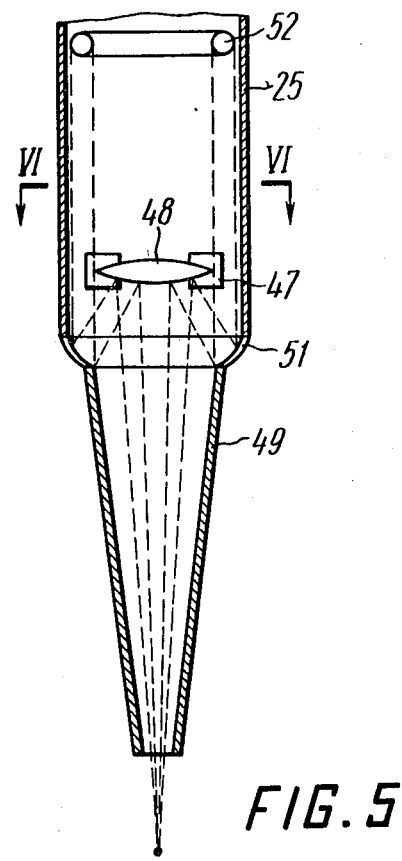
FIG. 5 shows a tip with a lens made of non-transparent materials and a visible light source, according to the invention.

The forementioned design of the flexible light guide 22 (FIG. 11) permits the surgeon to manipulate his tool, in this case the tip 49 (FIG. 3), and easy access to the prescribed point of the operation area 7 (FIG. 1) both perpendicular to the irradiated surface and at an angle thereto. The sterilized inert gas or gas mixture comes in the process of operation to the tip 49 (FIG. 3) under pressure through the pipe union 50. The apparatus is furnished with a set of tips 49 (FIGS. 3, 5 and 7). The first of them is intended for use in combination with the lens 48 transparent both for the laser beams and the beam of the simulation system 60 (FIG. 12). The second type of the tip 49 (FIG. 5) is designed for use with the lens 78 (FIG. 5) impermeable for the simulated beam. The third type of the tip 49 (FIG. 7) is for transformation of the laser beam into a cylindrical beam for irradiation of epithelial tissue of the viscera.

The emission of the lasers 1 and 98 (FIG. II) of the channel B is aligned with the help of the low-power lasers 96 and directed to the reflector 99 (FIG. II) of the optical switch 97 (FIG. 18). The reflector 99 has two positions: in the first position the reflector is off the optical axis of the channel B and the beam of the laser I passes into the channel unobstructed, in the second position the reflector is across the optical axis and deflects the beam of the laser 98 and sends it along the optical axis of the channel B. The change of positions of the reflector 99 (FIG. II) is effected by means of the electromechanical drive 100.

The beam further passes through the hole of the laser energy meter 101, warms up the hot junctions of the thermocouples placed in a circle along the perimeter of the laser beam. The thermal e.m.f. is measured by the instruments mounted in the central control panel 3 (FIG. 18) and the surgeon's panel 103.

A part of the beam falls further on the dividing plate 105 (FIG. II) and is fed to the reference measuring device 106 ensuring periodic calibration of energy characteristics of the lasers I and 98.

The laser beam simulation system 107 (FIG. 18) placed before the scanning device 9 comprises the retractable reflector 109 (FIG. II). This reflector is introduced into the channel B before the pumping of the laser and it sends the simulated beam along the optical axis of the channel B. When the pumping starts the reflector is automatically removed from the optical axis of the channel B and the laser beam comes to the reflectors 10 (FIG. II) positioned on different basic platforms for longitudinal travel II and for the cross travel 12 respectively, the platforms being moved horizontally with the respective drives 13 and 14 along the perpendicular rails 15 and 16. The reflector 10 placed on the cross travel platform 12 delivers the laser beam to the focusing barrel 8 (FIG. 18). The focusing barrel is adjusted by rotation of the handle 90 (FIG. 17) and the sliding rule 88 (FIG. 15) of the range finding device is set to the height corresponding to the estimated dimensions of the focused laser beam, the characteristics being read directly from the scale of the rule 88. Then the outer cylinder 77 of the focusing barrel 8 (FIG. 18) is lowered by means of the electromechanical drive 86 until the end of the slide rule 88 touches the operation area 7 (FIG. I). The outer cylinder 77 (FIG. 15) of the focusing barrel 8 may be lifted or lowered by hand, if the drive 86 (FIG. 15) is cut off by the buttom 93 actuating the lever drive 94 of the split nut 95 disconnecting the electromechanical drive 86 and the drive screw 80 (FIG. 15).

The unbalanced mass of the outer cylinder 77 is counterbalanced by the weight 83 suspended on the wire 84 over the roller 85 to the other cylinder 77.

The electromechanical drive 86 of the focusing barrel 8 (FIG. 18) is controlled from the control panel 3 and the surgeon's panel 103.

The proposed apparatus for laser therapy provides a means for simultaneous or alternate application of one or several lasers in different modes of operation and may be employed both for therapeutic purposes in the field of clinical medicine and for varius biological, physical and technical experiments.

Combination of CW laser emission to dissect tissue in surgery and irradiation by powerful laser emission in one apparatus furnishes unique conveniences for surgeons performing operations.

What is claimed is:
1. An apparatus for laser therapy, comprising:
   at least one laser for emission of laser energy;
   an emitting head of said laser;
   a power unit of said laser designed for excitation of said head of said laser;
   a control system of said power unit of said laser;
   a support mounting said laser;
   a scanning device positioned after said laser downstream of the laser beam permitting control of the laser beam in the operation area; said scanning device comprising two reflecting members: a horizontal longitudinal travel platform with one of said reflecting members placed thereupon and a horizontal transverse travel platform with the second reflecting member placed thereupon; perpendicularly arranged rails for said platforms to run upon;
   the forementioned elements of said scanning device permitting travel of the laser beam along the optical axis of the scanning device whatever the position of said barrel in the operation area;
   a barrel focusing the laser beam at a prescribed point of the operation area, positioned upon said horizontal longitudinal travel platform;
   said laser, scanning device and barrel making up a channel of the laser beam emission action.
2. An apparatus for laser therapy, comprising:
   at least one laser intended for emission of laser energy;
   an emitting head of said laser;
   a power unit of said laser designed for excitation of said head of said laser;
   a control system of said power unit of said laser;
   a support mounting said laser;
   a scanning device positioned after said laser downstream the laser beam and permitting control of the laser beam in the operation area; said scanning device comprising two reflecting members: a horizontal longitudinal travel platform with one of said reflecting members placed thereupon and a horizontal transverse travel platform with the second of said reflecting members placed thereupon; perpendicularly arranged rails for said platforms to run on; two additional reflecting members and an additional horizontal
   transverse travel platform placed upon said rails; said additional horizontal transverse travel platform carrying one of said additional reflecting members, whereas the second of said additional reflecting members is mounted upon said longitudinal travel platform;

a barrel focusing the laser beam at a particular point of the operation area, positioned upon said horizontal transverse travel platform;

a flexible light guide intended to delivery and focusing of the laser beam at a particular point of the operation area and positioned upon said additional transverse travel platform;

the forementioned laser, additional reflecting members positioned separately upon the additional transverse travel platform and the longitudinal travel platform of said scanning device, as well as said flexible light guide making up a channel of surgical action by the laser beam upon the object of irradiation, and same parts of the scanning device permitting travel of the laser beam along the optical axis of this channel whatever the attitude of said flexible light guide.

3. An apparatus for laser therapy as claimed in claim 2, wherein a locking device is provided on said additional transverse travel platform to secure rigid connection of this platform with said longitudinal travel platform for joint movement of both platforms.

4. A flexible light guide of an apparatus for laser therapy as claimed in claim 2, comprising:
hollow cylindrical light guides;
at least two joints placed between said cylindrical light guides to interconnect them;
bearings placed in said cylindrical light guides and joints to ensure mobility of said light guide;
laser beam reflectors placed on said joints;
at least two alignment platforms mounted on said bearings in the joints, wherein said reflectors are placed;
a link-and-lever swinging mechanism of said alignment platforms with said reflectors, intended for passing the laser beam along the optical axis when said cylindrical light guides and joints are in relative motion;
a focusing device placed in the last cylindrical light guide to provide for focusing of the laser beam in the operation area;
detachable tips attached to the focusing device end facing said operation area and designed to deliver the focused laser beam to various parts of the operation area.

5. A flexible light guide as claimed in claim 4, comprising at least two compensating springs for each of said joints, the ends of said spring being secured to a respective cylindrical light guide articulated by said joint, said compensating springs holding the cylindrical light guides in a position wherein said laser beam reflectors are set in said joints at an angle of almost 45° to the optical axis.

6. A flexible light guide as claimed in claim 4, comprising a laser beam simulation system made as a visible light source placed in said cylindrical light guide and having a shape of a ring and intended for visualization in the visible part of the spectrum of invisible laser emission.

7. A flexible light guide as claimed in claim 6, wherein said tip, when a focusing device impemeable to visible light is used, is a truncated cone facing the operation area with its narrow end, the connection of its wide end with said focusing device being made as a ring with a mirror-coated internal surface.

8. A flexible light guide as claimed in claim 4, wherein said tip for treatment of epithelial tissue of the viscera comprises:
a cylinder transparent for the laser emission;
a cone-shaped reflector placed within said cylinder so that its apex faces the incident laser beam, the apex angle of said cone being chosen depending on the density of energy of the laser beam passing therethrough required for irradiation.

9. A flexible light guide as claimed in claim 4, wherein said tip comprises a pipe union for supply of sterile gas mixture to the point of contact of the laser beam with biological structures, thus creating a sterile zone around the operation area, permitting more effective dissection of tissue, and protecting the focusing device against fouling by the products of the laser beam interaction with biological structures.

10. An apparatus for laser therapy as claimed in claim 1, comprising an optical switch, when several lasers differing in the nature of emission and their action on biological objects, this switch being placed at the point of intersection of their beams and intended for directing the emission of said lasers along the optical axis of the system.

11. An apparatus for laser therapy as claimed in claim 1, wherein the barrel for focusing the laser beam is made telescopic and comprises an additional drive for vertical travel.

12. An apparatus for laser therapy as claimed in claim 10, wherein said laser beam focusing barrel comprises a range finding device.

13. An apparatus for laser therapy as claimed in claim 11, wherein said range finding device is made as a rule arranged upon said barrel so that it can slide thereupon and measure the distance to the prescribed point of the operation area.

14. An apparatus for laser therapy as claimed in claim 1, including a suction system to remove the products of interaction between the laser radiation and biological objects, comprising:
intake flexible nozzles directed towards said operation area;
an air manifold connected with said hoses and ensuring suction of air from said operation area.

15. An apparatus for laser therapy as claimed in claim 2, comprising a suction system to remove the products of interaction between the laser radiation and biological objects, comprising:
intake flexible nozzles directed to said operation area;
an air monifold connected with said hoses and ensuring suction of air from said operation area.

16. An apparatus for laser therapy as claimed in claim 1, with a television system comprising:
a television camera hinged to said scanning device and directed towards the irradiated zone of said operation area permitting remote control of irradiation process during the operation;
a vidicon of said camera featuring shutters closing said vidicon at the moment of the laser beam flash, said shutters being provided with an electromechanical drive.

* * * * *